United States Patent [19]
Wittek

[11] Patent Number: 5,760,873
[45] Date of Patent: Jun. 2, 1998

[54] PROCESS AND DEVICE FOR THE SYNCHRONOUS ADDITION OF ODOURS TO VISUAL AND/OR ACOUSTIC STIMULATION

[76] Inventor: Götz-Ulrich Wittek, 500 Chesham House, 150 Regent Street, London, England, W1R 5FA

[21] Appl. No.: 537,937

[22] PCT Filed: Apr. 26, 1994

[86] PCT No.: PCT/EP94/01314

§ 371 Date: Dec. 12, 1995

§ 102(e) Date: Dec. 12, 1995

[87] PCT Pub. No.: WO94/26375

PCT Pub. Date: Nov. 24, 1994

[30] Foreign Application Priority Data

May 5, 1993 [DE] Germany .................. 43 14 886.7

[51] Int. Cl.⁶ ............... G03B 21/32; A62B 7/08; A47C 7/62
[52] U.S. Cl. .................. 352/85; 422/124; 422/125; 297/217.3
[58] Field of Search ............... 422/5, 125, 124; 297/217.3; 352/85; 472/59, 65

[56] References Cited

U.S. PATENT DOCUMENTS

| | | | |
|---|---|---|---|
| 2,540,144 | 2/1951 | Stern | 352/85 |
| 2,562,959 | 8/1951 | Stern | 352/85 |
| 3,628,829 | 12/1971 | Heilig | 297/217.4 |
| 3,795,438 | 3/1974 | Westenholz et al. | |
| 4,603,030 | 7/1986 | McCarthy | |
| 4,629,604 | 12/1986 | Spector | |

FOREIGN PATENT DOCUMENTS 10 59 038  2/1992  China.

Primary Examiner—W. B. Perkey
Attorney, Agent, or Firm—Burns, Doane, Swecker & Mathis, L.L.P.

[57] ABSTRACT

In a process for increasing the sensual perception of visual and/or acoustic stimulations, especially in cinemas, theatres, concert and lecture halls and in slide shows, videos, television transmissions, audio games and the like, the viewers or listeners are offered suitable odors synchronously with the provision of certain visual and/or acoustic stimulation. The odors passed to the viewers or listeners by a stream of vehicle gas are heated before the discharge of the vehicle gas in the air surrounding the viewers or listeners to an odor-specific temperature which ensures that the odoros or aromatic substances are appreciated.

12 Claims, 3 Drawing Sheets

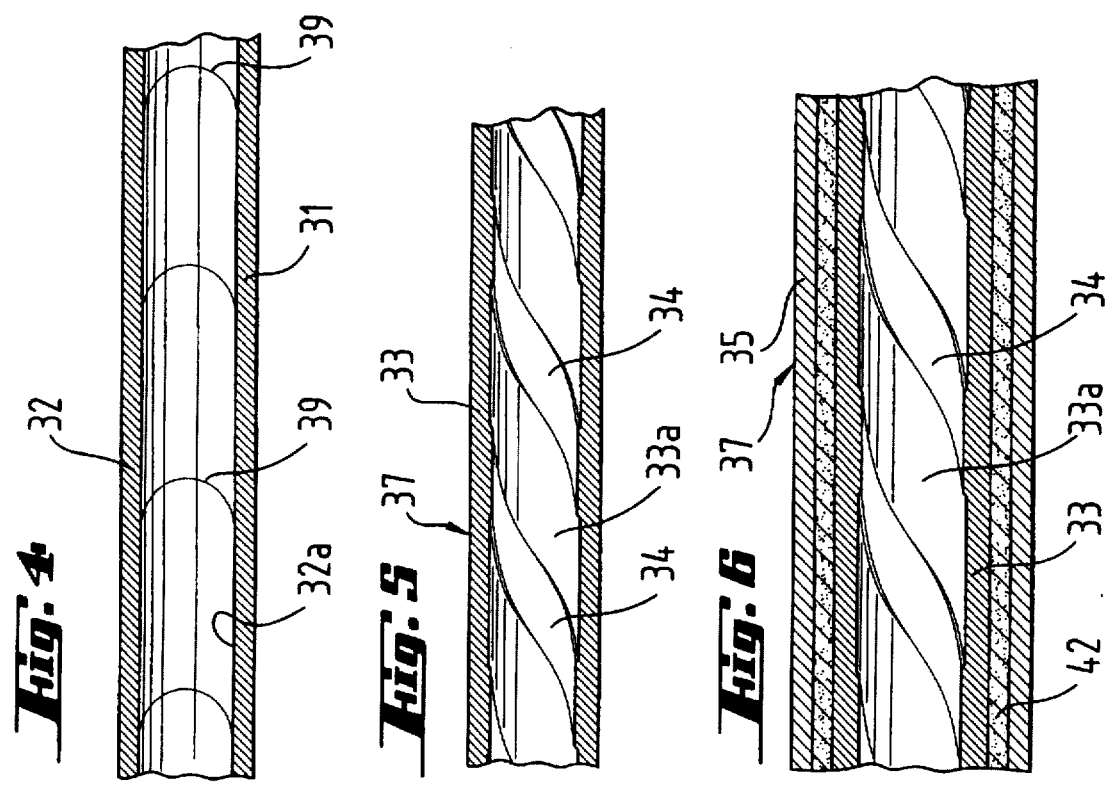
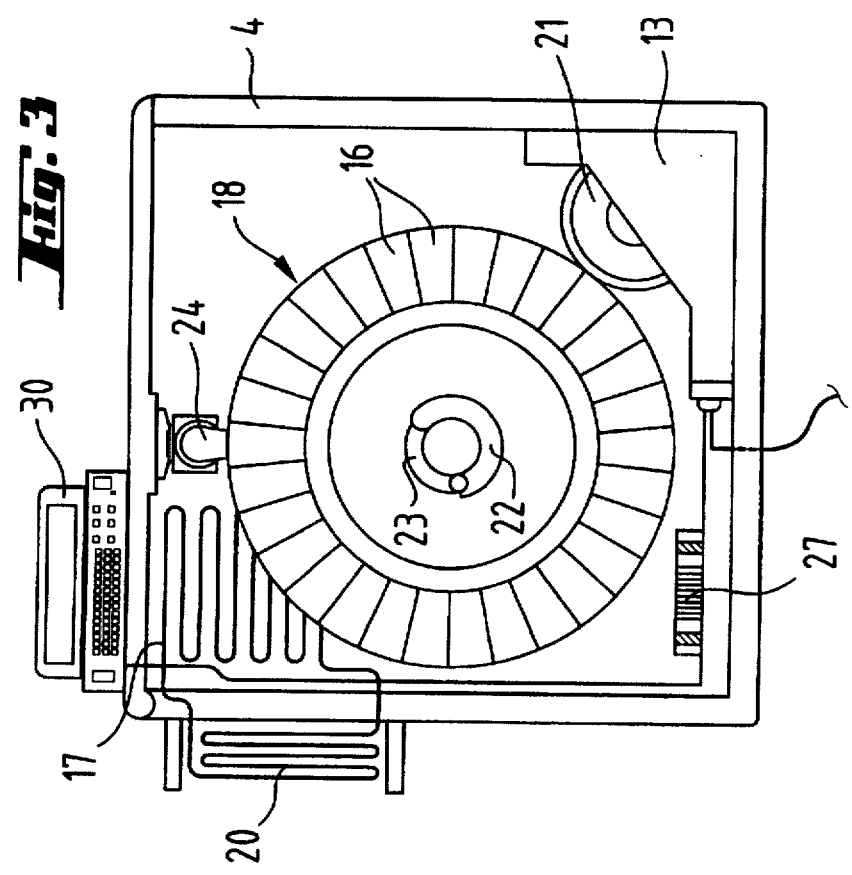

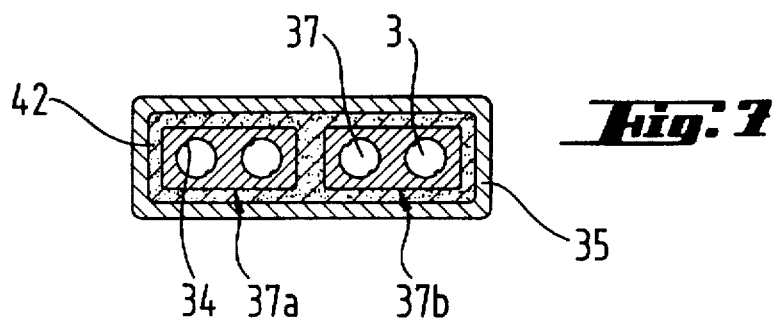
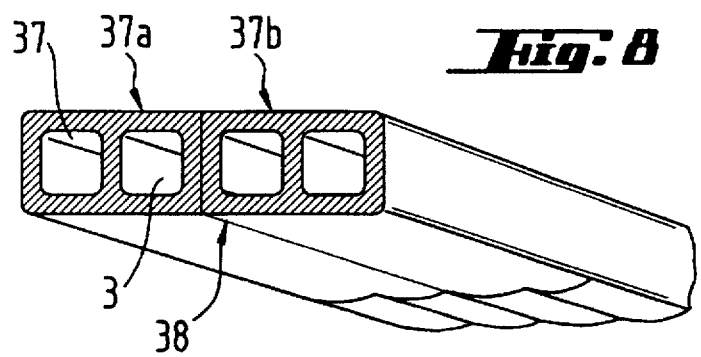
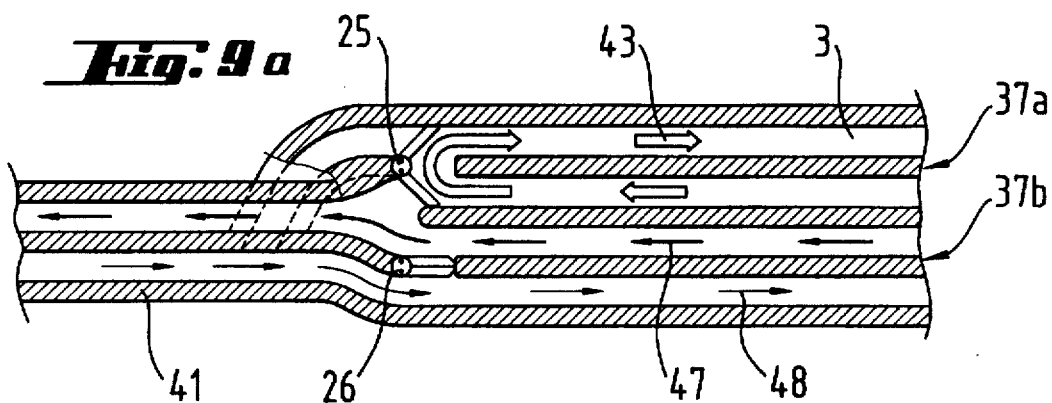
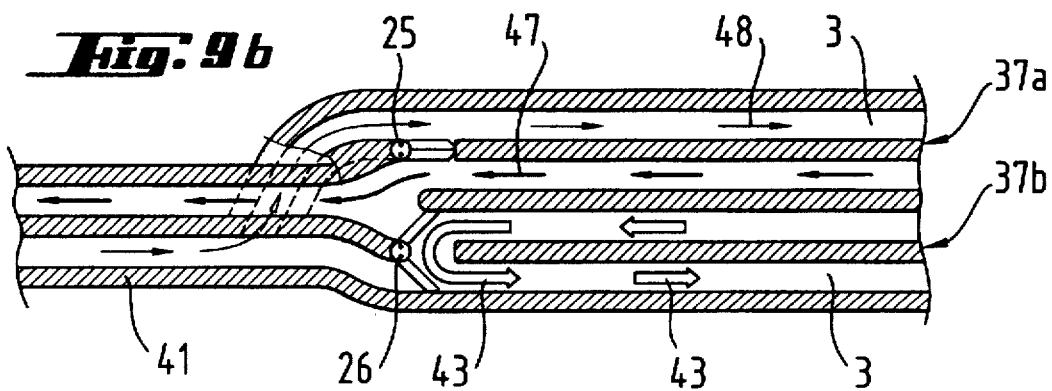

PROCESS AND DEVICE FOR THE SYNCHRONOUS ADDITION OF ODOURS TO VISUAL AND/OR ACOUSTIC STIMULATION

BACKGROUND OF THE INVENTION

The invention relates to a process and a device for adding odours or scents synchronously to visual and/or acoustic stimuli.

The invention relates to a process and a device for intensifying the sensorial perception of visual and/or acoustic presentations, in particular in cinemas, theaters, concert and conference halls, as well as during slide and video shows, television and radio broadcasts and the like, the audience being provided with scents corresponding to, and synchronous with, specific visual and/or acoustic events or scenes. A process and pertinent devices of this kind have been described in the applicant's German Patent Application No. P 41 35 796.5.

The present invention is primarily based on the object of improving a process and a device of this kind such that the characteristics of the scents used in the process can be perceived even better and are altered as little as possible.

SUMMARY OF THE INVENTION

This object is solved according to the invention by subjecting the scents to a scent-specific thermal treatment.

Thanks to the scent-specific thermal treatment, scents can be realized perfectly and true to nature for the first time.

Besides, it is possible by way of the invention to maintain the quality of the scents or odours used without any alteration and to avoid unwanted ageing and changes caused by the conduit system.

The invention provides a scent or aroma heating system as well as a conduit system for aroma cinemas and for projection apparatus used for cinematographic or other performances, which make it possible to provide scents exactly in correspondence with specific scenes.

SUMMARY OF THE INVENTION

According to a preferred embodiment of the process of the invention intended to intensify the sensorial perception of visual and/or acoustic presentations, the scents conveyed to the audience via a stream of carrier gas are heated to scent-specific temperatures before the carrier gas is released into the ambient air in the auditorium; said scent-specific temperatures are required in order that the perfumes and aromas may come to bear. Hence, certain scents which, after being produced, were impossible to realize because temperatures were too low can now be presented publicly for the first time.

In this process, the carrier gas is preferably heated to the scent-specific temperature, suitably before it gets into contact with the respective scent or aromatic substance. Alternatively, the carrier gas may be heated after contacting the aroma, which is preferably effected in the conduit system.

A temperature drop in the conduit system can be reliably prevented by heating the carrier gas to the scent-specific temperature just before it is released into the ambient air in the auditorium.

In order to prevent scents from adhering to the conduits and superimposing some other scent desired at that moment, the conduits are regularly purged, preferably by intermittently conveying the aroma-laden carrier gas and a purging gas through the ducts to the auditorium. The carrier gas charged with the aroma and the purging gas are suitably conveyed in pulse-like successive intervals so that a quasi permanent purging process is effected.

In a particularly favourable embodiment, the carrier gas contains helium or consists of helium. In this case, a film scent system is obtained in which helium heated to a temperature appropriate for the respective scent is used to develop the characteristics of said scent and in which the scent can also be quickly removed from the spectator's seat. In order to save helium, empty chairs in the aroma cinema are automatically cut off from the scent stream.

For reasons of cost, air—preferably compressed air—which may be additionally heated is used as purging gas.

It is important, particularly in a film scent system, to delay ageing of the aromatic substances in order to ensure the quality of the scent perceived by the audience. For this purpose, it is suggested that, in order to prevent ageing, the scents or aromas be cooled until they come into contact with the carrier gas. Such cooling may be effected in a deep cooling process.

So as to prevent the aromatic substances from adhering to the conduit walls during the passage through the conduit system, the carrier gas and/or the purging gas is/are suitably subjected to a constant rotary whirling motion, preferably a constant spiral rotary motion, in the conduit system leading to the audience.

According to another preferred aspect of the invention, a device is provided, particularly for carrying out the aforedescribed process, which comprises multiple conduits leading to the audience, at least one of said conduits being available, in alternating manner, for the supply of scent and another for the purging operation. Thus a purging system for scent supply conduits is achieved, which can also operate during the showing of a motion picture. This arrangement is preferably realized in the form of a twin system in which one system conveys scents to, and evacuates unwanted scents from, the spectator whereas the other system carries out the purging operation and can be used again as soon as aromatic substances settle in the first system.

This objective can also be achieved on the basis of multiple systems in which the conduits last used are purged and operation is switched to the other, available conduits. Alternatively, a purging system can be provided in which air (optionally heated) is passed through the conduits when no scents are supplied to the audience.

It has also proved useful for the device to contain a cooling means which cools the at least one scent or aroma reservoir.

The heating system for the aromatic substances preferably used in so-called aroma cinemas has to be designed such that the individual scents can be heated differently, i.e. according to their nature and the scent-related technical requirements. For such scent-specific heating, at least one controllable heating means for heating the carrier gas is preferably used.

A heating means is preferably provided such that the carrier gas is heated before it comes into contact with the at least one aroma. Alternatively, or additionally, a heating means may be provided adjacent each of the at least one scent discharge opening(s) located in the auditorium, which can preferably be adjusted individually. Heat loss in the transport system is thus reliably prevented.

Furthermore, a heating means can be provided between the at least one scent or aroma reservoir and the at least one scent discharge opening.

So as to reduce scent deposits in the conduit system, the conduits used for the transport of scents comprise at least at the inside a layer of inert material, preferably of glass or ceramics. In an advantageous embodiment, the conduits used for the transport of scents are designed completely as glass or ceramic conduits.

Aroma deposits at the conduit walls are also counteracted by means of spiral projections or projections having a similar effect at the inner walls of the conduits used for the transport of scents, or by designing said conduits in the form of spirals.

Further details regarding the design of the device and the process can be seen from the applicant's U.S. application No. 08/232,050 which is incorporated herein by reference.

BRIEF DESCRIPTION OF THE DRAWINGS

In the following, the invention is further explained with reference to the figures.

FIG. 3 shows a cooling and drying system for film scent reservoirs;

FIG. 4 shows a longitudinal section of a scent supply conduit having a common flow profile;

FIG. 5 shows a longitudinal section of a scent supply conduit which is spirally shaped at the inside;

FIG. 6 shows a longitudinal section of a buffered and armoured scent glass pipe which is spirally shaped at the inside;

FIG. 7 shows a cross-section of a double twin conduit including a purging system;

FIG. 8 shows a cross-section of another embodiment of the supply conduit system of FIG. 7;

FIG. 9a shows a cross-section of the double twin system of FIG. 8, the first conduit being switched to the purging state;

FIG. 9b shows a cross-section of the double twin system of FIG. 8, the first conduit being switched to the scent conveying state;

DETAILED DESCRIPTION OF THE PREFERRED EMBODIMENTS OF THE INVENTION

Figure 1:
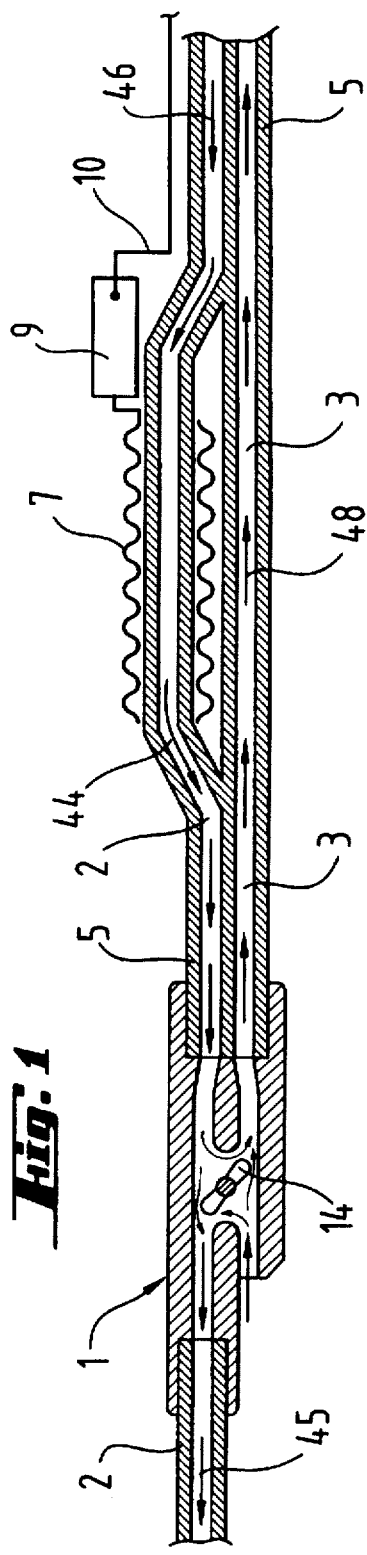
FIG. 1 shows a scent-specific heating and control system for aroma cinemas.

The embodiment of the invention as illustrated in FIG. 1 shows a scent heating and controlling system for the introduction of scents during motion picture shows, etc., which consists of a control unit 1 comprising a twin conduit 5 consisting of a scent supply conduit 2 and a return conduit 3, as referred to in the afore-mentioned application No. PCT/EP92/02446 incorporated herein.

In the present embodiment of the invention, the control unit 1 is again provided directly at the cinema viewing chair, the scent-charged quantities of air introduced being in the micro-range beyond existing air-conditioning technology, preferably between 0.2 and 0.0002 l/sec.

The control unit 1 enables the individual viewer to preset the intensity of scent impressions conveyed in correspondence to the movie scenes via the scent supply conduit 2 by way of the conduit controlling means 14 according to his/her own liking. Excess scent-charged air is fed into the return conduit 3 via the conduit controlling means 14.

In the above-referenced application, it has already been suggested for physical reasons that the scents discharged at the individual seats be heated to 3 to 4 degrees above air temperature in the cinema. This should lead to a recondution in the specific gravity of the discharged scent/air mixture; the scent last emitted immediately rises towards the ceiling of the cinema or the air-conditioning system so that superposition of scents of several movie scenes is avoided.

According to the present application, scents relating to different scenes are separated a lot more effectively when helium is added or used in pure form as scent transport medium, as will be described in more detail below.

Apart from the physical properties, a certain way of heating the emitted aroma quantities, via air, helium or other transport media, entails another, very important aspect regarding aroma technology.

The fascination of a movie being accompanied by scents often depends on the extent to which the complete spectrum of an aromas can be perfectly produced. Many aromas only develop their essential characteristics at specific temperatures. Often scents and aromas cannot be perceived or recognized without the specific effects of temperature; this is a problem frequently encountered by manufacturers or aromatic substances, who are usually not able to control the temperature at which a scent or aroma is applied. So it happens that certain aroma features can be generated under specific, ideal temperature conditions but cannot be reproduced in the concrete case of application.

In the present case, where scents are controlled by film and, as already mentioned, preferably transported by micro quantities of helium, it is possible for the first time to also provide the ideal temperature profile of the scents, thus making them accessible for consumers for the first time.

As illustrated in FIG. 1, a heating system 7 is provided at the scent supply conduit 2 before the control unit 1, said heating system being controlled via a heating control means 9. The heating control means 9 is connected to a pulse scanner (not shown) via a control cable 10.

Figure 2:
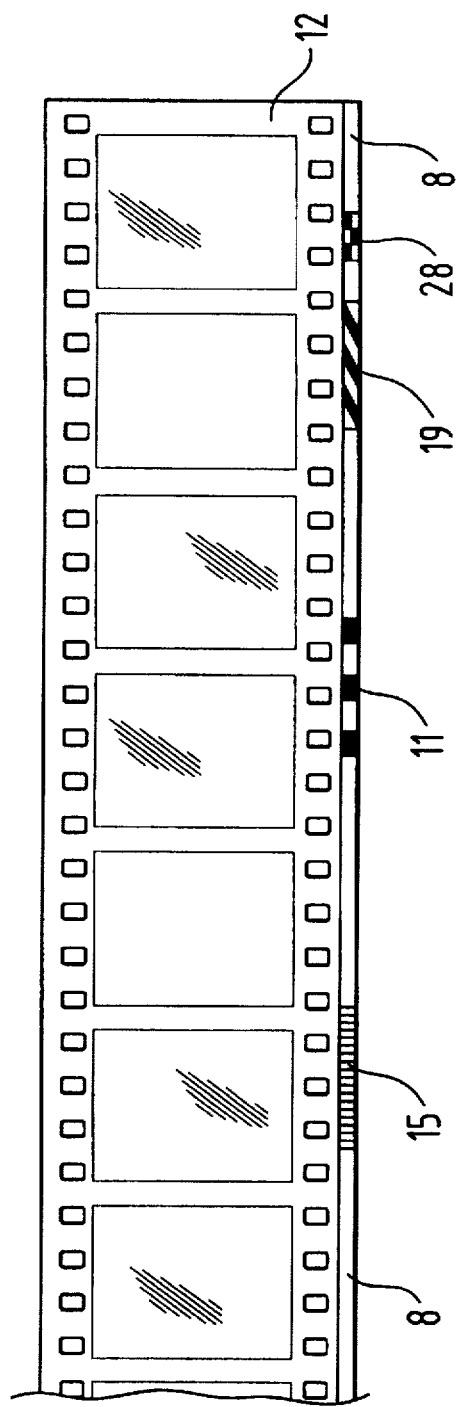
FIG. 2 shows a film strip with heat signals and control data.

During the showing of the movie, the pulse scanner reads data relating to the appropriate thermal value of a scent from a signal track 8 of the film stock 12 (FIG. 2). As the optimum temperature may vary from scent to scent, the respective scent-specific temperature signals 15 which trigger the heating system 7 are also arranged on the signal track 8 of the film (FIG. 2).

Depending on the design of the device, heating of the heating system 7 to the appropriate thermal value may take a few seconds, e.g. 3 seconds. For this reason, the associated temperature signal 15 is arranged at a correspondingly earlier position on the signal track 8 of the film stock 12 (FIG. 2) so that the thermal value pertaining to the desired scent and the associated movie scene are in synchronism.

In order to keep the heating step as short as possible, the surface of the supply conduit 2 is somewhat increased in the area of the heating system 7, e.g. by way of a flattened conduit, which also leads to a more rapid cooling of the heating system 7 in the case of successive lower thermal values.

Irrespective of other improvements of a scent's characteristics, the heating step may generally intensify the scent. In another embodiment (not shown), the heat level of the heating system 7 disposed at the spectator's seat can therefore be controlled to some extent by the conduit controlling means 14 which regulates scent intensity anyway.

In further embodiments of the invention (not shown), the heating system 7 may be incorporated in other positions of the scent supply system. It can be inserted at the start of a collective conduit for 10 seats and other positions of the distributing system, for instance.

If the heating system is positioned directly behind the central scent introducing system (not shown), the entire aroma cinema installation requires only a single heating system; in this case, the thermal values must increase with increasing distance of the heating system from the individual viewing chairs in order to compensate for heat losses in the conduit system.

In other embodiments of the invention which are designed in a basically similar way, helium is used as transport medium instead of minimized quantities of air. As helium is about seven times lighter than air, the introduced scents disappear quickly.

The particular advantage of this embodiment resides in the fact that the scents or aromas evacuate very quickly due to the inherent buoyancy of the transport medium so that no disturbing ventilator or the like is required.

Due to the extremely small amounts of gas used, superposition of scents in the audience is thus reliably prevented without any perceptible ventilation. This is very important, as the audience will not be distracted from the movie in any way.

Helium is excellently suited for this purpose, both with regard to health and safety regulations. It is non-combustible, chemically inert and completely harmless with respect to health; it has been used successfully for breathing apparatus of divers and breathing aids of asthmatics for decades.

The inner surfaces of the conduits and the conduit arrangement may have to be adjusted somewhat because of the considerably smoother and quicker flow of helium.

The quantities of helium required for scent transport are very small; nevertheless, thrifty use can be of advantage. According to an embodiment of the invention (not shown), seats that are not occupied during the showing of a movie are automatically disconnected from the scent stream so as to prevent expensive helium from being discharged unnecessarily. In a modified version, only the occupied seats are activated either manually by pushbutton or upon contact when a person sits down so that aromas and helium are only given off at the seats actually used.

The fascination of scents accompanying a movie does not only depend on the activation of the aroma available but also on the profile of an aroma whose particular characteristics have to be maintained.

For an aromatic impression to be considered credible and true to nature, the ageing process of the scent is often very important. To prevent the aromatic substances which at the time of discharge may have spent many weeks in the film scent reservoir of a cinema from ageing prematurely, the ambient temperature of the aromas to be stored is considerably decreased in the film scent reservoir 4 according to the embodiment of the invention as illustrated in FIG. 3.

The aromatic substances associated with individual scenes are contained in scent carriers 16 arranged on a scent roll 18. The scent roll 18 is rotatably mounted on a journal bearing 22 and secured by a journal securing means 23. The scent conduit leading to the viewers has access to all scent carriers 16 of the scent roll 18 via the scent connecting piece 24. The correct scent associated with a certain scene is triggered by scent pulses 11 arranged on the signal track 8 of the film stock 12 which are supplied to the scent roll controlling means 13. The scent roll controlling means 13 selects the appropriate scene-related aroma via the control wheel 21.

For reducing the ambient temperature of the aromas stored on the scent roll 18, a specific dry cooling system 17 is incorporated in the film scent reservoir 4. The dry cooling system adjusts the ambient air in the film scent reservoir 4 at coolness and moisture values optimally suited for all the scents on the scent roll 18; said values may vary slightly depending on the scent roll 18 and the film.

The specific coolness and moisture values of each scent roll 18 are reported to the central controlling means 30 via a data track (not shown) on the scent roll 18.

The appropriate coolness value is fed from the central controlling means 30 to the dry cooling system 17, the excess heat flowing to the external heat exchangers 20. The moisture which frequently collects during cooling steps and which may impair the quality of some aromas is controlled in the film scent reservoir 4 via a moisture controlling means 27 which is also controlled by the central controlling means 30.

The central controlling means 30 simultaneously controls all scent commands fed to the scent roll 18 via the scent controlling means 13, as well as all the commands used in the cinema, e.g. commands concerning valves, the heating process and the like.

The scents introduced in the conduit system from the scent carriers 16 of the scent roll 18 via the scent connecting piece 24 are delivered—in a most accurately electronically controlled process—to the individual spectator and are optionally activated by a heating system. If the heating system is a central heating system directly behind the scent inlet at the scent connecting piece 24, the required thermal energy may optionally be drawn by a correspondingly adapted heat exchanger of the cooling system.

FIG. 4, which illustrates an embodiment of a scent supply conduit, shows the type of flow profile in a scent supply conduit 31 (considerably enlarged) as intended in application PCT/EP92/02446 incorporated herein.

Said scent supply conduit 31 comprises a conduit wall 32 with a straight inner wall 32a and the flow profile 39 as it usually occurs in this connection. It can be clearly seen that the flow velocity of the air conveyed in said conduit sharply decreases at the inner walls 32a of the conduit.

This may lead to micro-particles, here: aroma particles, carried in the air flow being deposited on the edges of such conduits, as they are not sufficiently entrained by the slow marginal flow.

When aromas are given off for a rather long period of time, so many aroma particles may deposit on the conduit walls that a subsequent air flow without aromas, i.e. pure air, takes on the scent of previous aroma discharge(s) and carries said scent to the audience even after the relevant movie scene.

Likewise, previous aromas could mix with subsequent scents and cause a mixture of scents which the audience may find to be unpleasant and which would no longer correspond to the movie scenes. As a result, the audience would be irritated and distracted from the movie instead of experiencing it more intensely.

So as to overcome this drawback, the embodiment of the invention as illustrated in FIG. 5 (in enlarged form) which consists of a scent supply conduit 37 and a conduit wall 33 has inner surfaces 33a of specific design.

The inner surfaces 33a of the conduit wall 33 comprise elongated recesses or projections 34 designed to impart a continuous rotary motion on the air flowing therethrough. In the present embodiment, the recesses or projections 34 have the shape of a spiral line which slightly protrudes inwardly from the inner surfaces 33a of the conduit wall 33 and continues this way over the entire length of the conduit.

As the spirally arranged projections 34 impart a continuous spiral rotary motion on the air flowing through the conduit, the velocity of the air passing along the edges of the conduit is considerably increased and, depending on the design, may even exceed the velocity of the air flowing in the middle of the conduit.

The aroma particles entrained in the air stream are thus also strongly accelerated in the marginal layers of the stream, which prevents the aroma particles from depositing on the inner surfaces 33a of the conduit wall 33. The projections 34, here: a spiral line, are incorporated in the inner surface 33a of the conduit wall 33 during the manufacturing process. Shapes of this kind can also be obtained by deforming the conduit as a whole in a slightly torsional manner during the manufacturing process.

To prevent the formation of unwanted micro-turbulences behind the projections 34 (in the direction of flow) and thus the accumulation of aroma particles, the contours of the spiral projections 34 are relatively smoothly shaped.

Apart from the shape of the inner surfaces 33a of the conduit wall 33, the fine structure of said surfaces and a possible chemical reactivity of the material are important factors for the prevention of aroma deposits.

As regards the chemical reactivity with aroma particles, most plastics are reactive and therefore generally not suited for this field of application, in spite of their favourable processibility. In a preferred embodiment of the invention, the material used for the conduit wall 33 is a particularly inert type of steel, e.g. V4a steel.

Even ducts made of steel and other inert materials may cause problems, however. If the surfaces exhibit fissures or various minute indentations, for example (detectable by microscopic inspection), aroma particles will be more likely to settle than on very smooth surfaces.

According to another embodiment of the invention, shown in enlarged form in FIG. 6, particulary favorable materials, namely relatively elastic types of glass, are used for the conduit walls 33 of the scent supply conduits 37. Conduits made of glass have the smoothest surfaces in the microrange, so that aroma deposits are basically ruled out.

Such glass conduits can also be provided with structures, e.g. spiral projections 34, which impart a continuous rotary motion on the stream of air until the air is discharged at the viewer's seat.

In the special scent supply conduits 37 of the embodiment illustrated in FIG. 6, aroma deposits are prevented in two ways: the spiral-shaped course structure of the surface accelerates the air flowing in the marginal layers of the air stream to such an extent that the entrained aroma molecules are prevented from slowing down and adhering to the inner surfaces 33a, while the smooth fine structure of the inner surfaces 33a of the conduit walls 33 prevents aroma molecules from settling down even under the most unfavorable flow conditions.

It might be advantageous to protect elastic types of glass from external strains, too, particularly if they are not laid under the floor but are subsequently installed as microconduits above the floor of existing movie theaters. For this reason, the conduit walls 33 of the embodiment illustrated in FIG. 6 are additionally embedded in an elastic layer 42 which in turn is supported in a warp-resistant protective sleeve 35 which is made of hard plastics or high-carbon steel, for example.

In another embodiment of the invention as illustrated in FIG. 7, aroma deposits on the inner surfaces of the conduits are not primarily prevented by the surface properties of the conduits. Rather, two twin conduits 37a and 37b are used which are supported in an elastic layer 42 enclosed by the flat aggregate sleeve 36.

Of the two twin conduits only one, e.g. conduit 37a, is used for the supply of aromas. After certain intervals of predetermined length (based on experience), e.g. 60 functional minutes, when the onset of even the slightest aroma deposits can be detected, operation can be switched from twin conduit 37a to twin conduit 37b in the scent supply conduit 40.

When both twin conduits 37a and 37b have been used, the conduits can be purged as indicated in the original application, P 41 35 796.5, where a double conduit, e.g. 37a, is joined at the outlet opening.

Instead of air, a cleansing liquid is introduced in one of the two conduits of the twin conduit 37b, said liquid flowing through the whole conduit to the spectator's seat (not shown), changing over to the second conduit and subsequently flowing back to the compressor (not shown). In this process, both individual conduits of the twin conduit 37b are cleaned at the same time, while immediately afterwards warm air for drying passes therethrough.

If both twin conduits 37a and 37b of the embodiment of the invention according to FIGS. 7, 8, 9a and 9b are expected be used up during a motion picture show, it is also possible—due to the very small conduit diameters and the relatively low pressure—to clean one of the two twin conduits without perceptible noise during the show while the other twin conduit is further used for conveying scents. Due to the very small volumes involved, such a cleaning step can be effected in about 0.5 to 3 minutes.

If, according to this embodiment, cleaning shall be effected during a show, the twin conduits 37a and 37b are preferably combined to a functional block 38 in the final portion at the spectator's seat, and the conduit cross-sections are preferably changed from round to rectangular shapes (FIG. 8).

FIGS. 9a and 9b of the embodiment illustrated in FIG. 8 refer to the mode of operation of the final portion of the conduit if a conduit is to be purged during the showing of a movie. Two conduits of a twin conduit 37b are joined at the outlet opening, i.e. at the final portion of the conduit in the area of the spectator's seat, by means of end valves 25 or 26 which are electronically controlled and operate without noise.

If the end valve 25 is activated and the end valve 26 is deactivated, the twin conduit 37b can be further used for conveying aromas while the twin conduit 37a is purged (FIG. 9a). In this case, the conduit 37b extends into the final portion 41 of the conduit towards the spectator.

When aroma deposits are to be expected in the supply conduit of twin conduit 37b, valve 26 is activated and valve 25 deactivated during an appropriate scent interval. The aroma is then conveyed through the previously purged twin conduit 37a to the final portion of the conduit, and the twin conduit 37b is purged.

Such switching operations without noise can be effected by various types of valve and valve arrangements, e.g. by slide and lock valves, or valves which change over particularly slowly and in addition may be dampened.

All end valves 25 and 26 combined are actuated centrally, e.g. from the projectionist's cabin via radio or via a small electronic line which may be integrated in the scent supply system.

Noiseless valve operation guarantees that the motion picture show will not be disturbed when all valves, e.g. 500 valves in a 500—seat movie theater, are switched simultaneously. If it is not possible to avoid noise completely when switching a large number of valves simultaneously, the valves can be switched in segments, e.g. first for about 20% of seats, then for the next 20%, and so on.

Another measure to completely avoid even the slightest noise during the switching of valves or the subsequent purging operation is to carry out the switching and purging of a conduit exactly during a loud sequence of the movie. The noise pertaining to the movie then masks possible other noise. The signal 19 for triggering the switching and purging phase, which has to be arranged directly after the start of a loud movie sequence, is preferably located on the signal track 8 of the film where the other signals for aroma control are located, too.

Another measure for preventing aromatic substances from accumulating in the conduits is to purge the conduits with normal and, optionally, slightly heated air during all phases of the movie where no aromas are conveyed to the audience. For this purpose, a reversing valve (not shown) is provided directly after the scent reservoir from which the aromas are introduced in the conduits, i.e. within the projectionist's cabin.

The reversing valve is activated when there has been no introduction of scent for a specified period of time; it is deactivated as soon as aromas are fed into the system again.

List of Reference Numbers (1) control unit
(30) central controlling
(2) scent supply conduit
means
(3) return conduit
(31) scent supply conduit
(4) film scent reservoir
(32) conduit wall
(5) twin conduit
(32a) inner wall
(7) heating system
(33) conduit wall
(8) signal track
(33a) inner surfaces
(9) heating control means
(34) projections
(10) control cable
(35) protective sleeve
(11) scent pulse
(36) aggregate sleeve
(12) film stock
(37) scent supply conduit
(13) scent roll controlling means
(37a) twin conduit
(14) conduit controlling means
(37b) further twin conduit
(15) temperature signal
(38) conduit block
(16) scent carrier
(39) flow profile
(17) dry cooling system
(40) scent supply conduit
(18) scent roll
(41) end portion of
conduit
(19) purging signal
(42) elastic layer
(20) heat exchanger
(21) control wheel
(22) journal bearing
(23) journal securing means
(24) scent connecting piece
(25) end valve
(26) end valve
(27) air moisture controlling means

I claim:

1. Apparatus for intensifying sensorial perception of visual and/or acoustic presentations, particularly in cinemas, theaters, concert and conference halls, as well as during slide and video shows, television and radio broadcasts and the like, where the audience is supplied with scents in synchronism with the presentation of specific visual and/or acoustic stimuli, the apparatus including multiple conduits leading to the audience, at least one of which can be used for conveying scents and, alternately, at least one for purging, wherein the conduits used for conveying scents are glass or ceramic conduits.

2. Apparatus according to claim 1, characterized in that the conduits are designed as twin conduits.

3. Apparatus according to claim 1, characterized in that the conduits are designed as a multiple system.

4. Apparatus according to claim 1, characterized by a cooling means for cooling the at least one scent reservoir.

5. Apparatus according to claim 1, characterized by at least one controllable heating means for heating the carrier gas.

6. Apparatus according to claim 5, characterized in that a heating means is provided such that it heats the carrier gas before said gas comes into contact with the scent.

7. Apparatus according to claim 5, characterized in that a heating means is provided adjacent each of the at least one scent discharge opening(s) in the auditorium, which can preferably be controlled individually.

8. Apparatus according to claim 5, characterized in that a heating means is provided between a scent reservoir and the at least one scent discharge opening.

9. Apparatus according to claim 1, characterized in that the conduits used for conveying scents have spiral projections at the inner walls thereof.

10. Apparatus according to claim 1, characterized in that the conduits used for conveying scents extend in the form of a spiral.

11. Apparatus for intensifying sensorial perception of visual and/or acoustic presentations, particularly in cinemas, theaters, concert and conference halls, as well as during slide and video shows, television and radio broadcasts and the like, where the audience is supplied with scents in synchronism with the presentation of specific visual and/or acoustic stimuli, the apparatus including multiple conduits leading to the audience, at least one of which can be used for conveying scents and, alternately, at least one for purging, wherein the conduits used for conveying scents have spiral projections at the inner walls thereof.

12. Apparatus for intensifying sensorial perception of visual and/or acoustic presentations, particularly in cinemas, theaters, concert and conference halls, as well as during slide and video shows, television and radio broadcasts and the like, where the audience is supplied with scents in synchronism with the presentation of specific visual and/or acoustic stimuli, the apparatus including multiple conduits leading to the audience, at least one of which can be used for conveying scents and, alternately, at least one for purging, wherein the conduits used for conveying scents extend in the form of a spiral.

* * * * *